United States Patent [19]
Liboff et al.

[11] Patent Number: 5,143,588
[45] Date of Patent: * Sep. 1, 1992

[54] TECHNIQUES FOR ENHANCING THE PERMEABILITY OF IONS THROUGH MEMBRANES

[75] Inventors: Abraham R. Liboff, Birmingham, Mich.; Bruce R. McLeod, Bozeman, Mont.; Stephen D. Smith, Lexington, Ky.

[73] Assignee: Life Resonances, Inc., Bozeman, Mont.

[ * ] Notice: The portion of the term of this patent subsequent to Apr. 4, 2006 has been disclaimed.

[21] Appl. No.: 561,844

[22] Filed: Aug. 2, 1990

Related U.S. Application Data

[63] Continuation of Ser. No. 280,848, Dec. 7, 1988, which is a continuation of Ser. No. 923,760, Oct. 27, 1986, Pat. No. 4,818,697.

[51] Int. Cl.$^5$ .......................... C25B 5/00; C12N 13/00
[52] U.S. Cl. .............................. 204/155; 204/157.15; 204/180.1; 204/193; 435/173
[58] Field of Search ................ 204/155, 157.15, 180.1, 204/193; 435/173

[56] References Cited

U.S. PATENT DOCUMENTS 3,356,601 12/1967 Inoue .
4,818,697 4/1989 Liboff et al. ................... 204/157.15

FOREIGN PATENT DOCUMENTS 3825585 8/1985 Australia .

OTHER PUBLICATIONS

Liboff, et al., "Time-Varying Magnetic Fields: Effects on DNA Synthesis," Science 223:818-820 (1984).
Bawin, et al., "Possible Mechanism of Weak Electromagnetic Field Coupling in Brain Tissue," Bioelectrochemistry and Bioenergetics 5:67-76 (1978).

(List continued on next page.)

Primary Examiner—John Niebling
Assistant Examiner—Steven P. Marquis
Attorney, Agent, or Firm—Dykema Gossett

[57] ABSTRACT

A method is provided for enhancing the transport of a selected ion having a predetermined charge-to-mass ratio through a biomolecular membrane located in a space subjected to a local magnetic field. The space defines at least one reference path passing through the membrane in opposite first and second directions. The method includes the steps of creating a magnetic field which, when combined with the local magnetic field, produces a magnetic field having a flux density with at least one component representable by a component vector having a direction extending in the first direction along the path. This component of the magnetic field has a magnitude that fluctuates at a predetermined rate to produce a nonzero average value. A predetermined relationship between the ratio of the selected rate to the nonzero average value and the charge-to-mass ratio of the predetermined ion is thereby created. The predetermined relationship is a function of the cyclotron resonance frequency of the ion.

The present invention also provides an apparatus for enhancing the transport of a selected ion having a predetermined charge-to-mass ratio through a biomolecular membrane. The apparatus includes field creating means responsive to signals for creating a magnetic field which, when combined with the local magnetic field, produces a magnetic field having flux density with at least one component representable by a component vector having a direction extending along a path through the membrane and having a magnitude that fluctuates at a predetermined rate to create a nonzero average value. The ratio of the predetermined rate to the nonzero average value has a predetermined relationship with respect to the charge-to-mass ratio of the predetermined ion which is a function of the cyclotron resonance frequency of the ion. Signal generating means is provided for generating the signals, at least some of which are generated at the predetermined rate.

35 Claims, 5 Drawing Sheets

OTHER PUBLICATIONS

Lielmezs, et al., "External Transverse Magnetic Field Effect on Electrolyte Diffusion In LiCl–$H_2O$ Solutions," *Bioelectrochemistry and Bioenergetics* 5:285–295 (1978).

S. D. Smith et al, "Pulsed Magnetic Field Modulation of LSA Tumors in Mice," Journal of Bioelectricity, 1(2), 207–229 (1982).

S. D. Smith et al, "Effect of Prepetition Rate and Duty etc.," Journal of Electrochemistry, vol. 130, No. 3 121c (1983).

S. D. Smith et al. "Effects of Duty-Cycle Distribution etc., " Journal of Bioelectricity, 4(1), 15–41 (1985).

Barsoum et al, "Effects of Electromagnetic Radiation in the Range 20–300 MHz on the Vacuolar Potential of Characean Cells," Bioelectromagnetics 3:193–201 (1982).

Morita et al, "Near-Field Absorption in a Circular Cylinder From Electric and Magnetic Line Sources," Bioelectromagnetics 3:253–274 (1982).

Tenforde et al, "Cardiovascular Alterations in Macaca Monkeys Exposed to Stationary Magnetic Fields," Bioelectromagnetics 4:1–9 (1983).

Drago et al., "Frequency Dependence of An analytical Model of an Electrically Stimulated Biological Structure," Bioelectromagnetics 5:47–62 (1982).

B. R. McLeod et al. "Electromagnetic Fields Induced by Helmoholtz Aiding Coils Inside Saline-Filled Boundaries," Bioelectromagnetics 4:371–381 (1983).

Kinouchi et al., "Design of a Magnetic Field Generator for Experiments on Magnetic Effects in Cell Cultures," Bioelectromagnetics 5:399–410 (1984).

Adey et al, "Effects of Weak Amplitude-Modulated Microwave Fields on Calcium Efflux From Awake Cat Cerebral Cortex", Bioelectromagnetics 3:295–307 (1982).

Merritt et al, "Attempts to Alter $^{45}Ca^{2+}$ Binding to Brain Tissue with Pulse-Modulated Microwave Energy," Bioelectromagnetics 3:475–478 (1982).

Blackman et al, "Effect of ELF (1–20Fz) and Modulated (50Hz) RF Fields on the Efflux of Calcium Ions from Brain Tissue in Vitro," Bioelectromagnetics 6:1–11 (1985).

Abstracts from the Sixth and Seventh Annual Meetings, Jul. 1984 and Jul. 1985 of the Bioelectromagnetic Society.

"A Role for the Magnetic Field in the Radiation-Induced Efflux of Calcium Ions form Brain Tissue in Vitro," Bioelectromagnetics, 6:327–337 (1985).

A. R. Liboff, "Cyclotron Resonance in Membrane Transplant" *Interactions Between Electromagnetic Fields and Cells.*

A. R. Liboff, Geomagnetic Cyclotron Resonance in Living Cells, Journal of Bio. Physics, vol. 13, 1985.

Switch Position 26a

TECHNIQUES FOR ENHANCING THE PERMEABILITY OF IONS THROUGH MEMBRANES

This is a continuation of co-pending application Ser. No. 07/280,848 filed on Dec. 7, 1988, which is a continuation application of U.S. patent application Ser. No. 06/923,760 filed on Oct. 27, 1986, now U.S. Pat. No. 4,818,697.

BACKGROUND AND SUMMARY OF THE INVENTION

1. Field of the Invention

This invention relates to the transfer of ions through membranes, and more specifically relates to the electromagnetic alteration of biochemical activity in living cells.

2. Description of Related Art and Summary of the Invention

The biochemical and medical fields have long sought an inexpensive and accurate method of enhancing the movement of selected ions involved in life processes across living cells membranes. Until the discovery described in this specification, no investigator had found a satisfactory technique for achieving such results. The control of such ions has been achieved up to now solely by the administration of pharmaceutical agents which often entail invasive hazard and which at best are less than efficacious in their results. The applicants have succeeded where others failed because they have discovered the cause and effect relationship between certain types of extremely low frequency (ELF) magnetic fields and the movement of selected ions across the membranes of living cells.

The closest known related work is described by Blackman et al. in "A Role For The Magnetic Field In The Radiation-Induced Efflux Of Calcium Ions From Brain Tissue In Vitro," 6 *Bioelectromagnetics* 327-337 (1985). Blackman et al. noted changes in the efflux of calcium ion from brain tissue in response to various magnetic fields. Since Blackman et al. used tissue specimens rather than single cells, it is impossible to tell whether the efflux of calcium ions noted by them was due to a cell membrane response as opposed to movement of ions in bulk interstitial fluids or in damaged cells.

Blackman et al. used both a constant unipolar magnetic field and a fluctuating bipolar magnetic field arranged perpendicular to each other. The fluctuating bipolar field was generated by a transmission line. According to conventional field theory, the transmission line produced magnetic flux lines arranged in concentric rings around the axis of the line. Blackman et al. noted modest calcium efflux (e.g., 20 to 30% increase when compared to controls) when the constant and fluctuating fields were perpendicular, but failed to note any efflux for any other orientation of the fluctuating field and constant field (p. 334). Furthermore, according to the *BEMS Seventh Annual Meetings Abstracts* (1985), Blackman et al. ruled out a simple cyclotron resonance model as the underlying causative mechanism for their observations.

Contrary to the observations of Blackman et al., the applicants have discovered that they can substantially increase the permeability of a selected ion through a membrane subjected to either the earth's geomagnetic field or to an arbitrarily chosen static magnetic field by superimposing a fluctuating magnetic field with a flux density having a nonzero net average value that is properly proportioned with respect to the frequency of the the fluctuations. The applicants have succeeded by creating a magnetic field which, when combined with either the earth's geomagnetic field or an arbitrarily chosen static magnetic field, results in a magnetic field having at least one rectangular component extending along an axis projecting through the cell and having a magnitude that fluctuates at a prescribed predetermined rate to create a nonzero average value. The field is generated so that the ratio of this predetermined rate to the nonzero average value is limited by means of a predetermined relationship with respect to the charge to mass ratio of the predetermined ion.

According to a preferred practice of the invention, the predetermined rate (in Hz) times $2\pi$ is substantially equal to the charge-to-mass ratio (in Coulombs per kilogram) of the predetermined ion times the nonzero average value of magnetic flux density (in Tesla). This is a relationship of the type rejected by Blackman et al. and hereafter called the "Cyclotron Resonance Relationship":

$$2\pi f_c = \left(\frac{q}{m}\right)B$$

By properly orienting and controlling the resultant magnetic field, the applicants have discovered that the cyclotron resonance can be used to enhance the transfer of a selected ion across the membrane of a living cell. This technique enables the applicants to alter the transfer of some ions by a substantial factor up to ten or more times greater than would occur normally, or by any other technique. By using this technique, the influx or efflux of selected ions from living cells can be regulated economically with a degree of precision and speed previously unknown.

DESCRIPTION OF THE DRAWINGS

These and other advantages and features of the invention will hereafter appear for purposes of illustration, but not of limitation, in connection with the accompanying drawings, wherein like numbers refer to like parts throughout, and wherein.

DESCRIPTION OF THE PREFERRED EMBODIMENTS

When used in the present application and claims: "B" represents Magnetic Flux Density measured in Tesla (1 Tesla = $1 \times 10^4$ gauss). B is also often referred to as Magnetic Induction or Magnetic Field (see P. A. Tipler, *Physics*, 2nd ed., p. 723, Worth Publishers, Inc., 1982, New York).

"m" represents ionic mass, measured in kilograms.

"q" represents ionic charge, measured in Coulombs.

"f" represents frequency, measured in Hertz.

"$f_c$" represents cyclotron resonance frequency, measured in Hertz.

"Helmholtz coils" refers to a coaxial configuration of a pair of equal electrical coils, each having the same number of total turns of wire, with the mid-planes of the two coils separated by a distance equal to the radius of either coil, with the two coils wound and electrically connected such that the magnetic flux density from each coil at the point on the axis halfway between the coils points in the same direction.

"Local magnetic flux density" refers to the ambient magnetic field that is substantially constant in time and omnipresent in all environments. This will include the earth's geomagnetic field as it occurs naturally or altered levels of the earth's field that result from the presence of local magnetic materials or the energization of electrical coils for the purpose of augmenting or decreasing the earth's geomagnetic field.

"Active volume" is the working volume within the region defined by a set of Helmholtz coils, or a solenoid, or any other arrangement of electrical coils or permanent magnets, used in conjunction with the local magnetic field, to create a net magnetic flux density. The magnetic flux density everywhere within the active volume is predictable, measurable and uniform, (i.e., substantially equal everywhere within this volume). The active volume, in the present case, encompasses the total volume of cell or tissue that are exposed to the magnetic flux density required in the preferred practice of this invention. The magnetic flux density over the total volume of exposed cells or tissue will thereby be substantially the same.

Referring to the drawings, the transfer of a predetermined ion through a membrane can be dramatically enhanced by a variety of magnetic flux densities. Three preferred arrangements for achieving such flux densities are shown schematically in FIGS. 1, 4 and 6.

Figure 1:
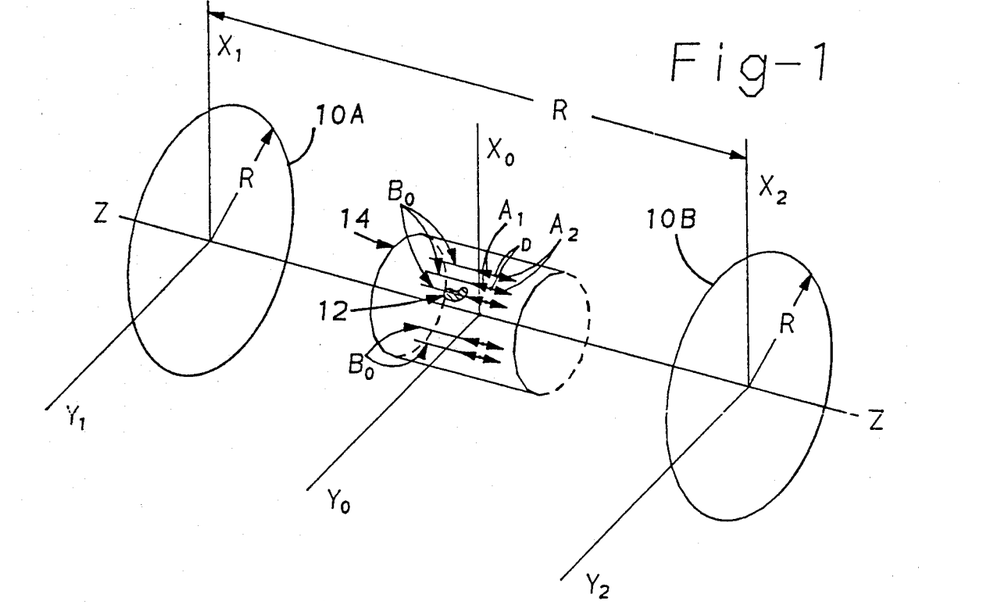
FIG. 1 is a schematic, perspective view of an exemplary living cell located in a bounded active volume in a space defining a rectangular coordinate axis system and subjected, within this active volume, to a magnetic flux density created by an electrical coil, or an equivalent permanent magnetic array or any other equivalent source of magnetic flux density, such as the earth's geomagnetic field.

Referring to FIG. 1, coils 10A and 10B of a conventional Helmholtz coil pair having N turns of wire making a loop with diameter 2R, have a longitudinal axis identified by the letter Z (FIG. 1). The mid-planes of each coil, located at $X_1Y_1$ and at $X_2Y_2$ are separated by a distance R. (The scale in the direction of the Z-axis has been expanded to more clearly show volume 14.) One such coil pair has 500 turns of No. 24 wire on each loop, with a 23 centimeter diameter for each loop; the two loops are separated by 11.5 centimeters. Helmholtz coils are described in Scott, *The Physics of Electricity and Magnetism* (John Wiley & Sons, Inc. 1962) at p. 315. The number of turns N, the diameter of the coils 2R, the separation of the coils R, and the wire gauge are only critical insofar as conventional practice requires constraints on these and other design parameters to allow optimal performance characteristics in achieving predetermined flux densities as required in the preferred practice of the present invention. These predetermined flux densities may also be achieved by conventional devices other than Helmholtz coils, such as solenoids, electromagnets, and permanent magnets.

Whatever the means of generating this flux density, the essential aspect relevant to this invention is that a predictable, measurable and uniform magnetic flux density having the value $B_o$ be established everywhere within active volume 14, and that this active volume will encompass the total volume of cells and/or tissue that are exposed to this flux density $B_o$. A unipolar vector representing magnetic flux density $B_o$ is pictured in FIG. 1 with arrows A1 and A2 separated by a "." that represents the average nonzero value of the vector. The opposed arrows represent the fact that the magnitude of $B_o$ changes at a predetermined rate. For purposes of illustration, a single exemplary living cell 12 is pictured in FIG. 1 within active volume 14.

Figure 2:
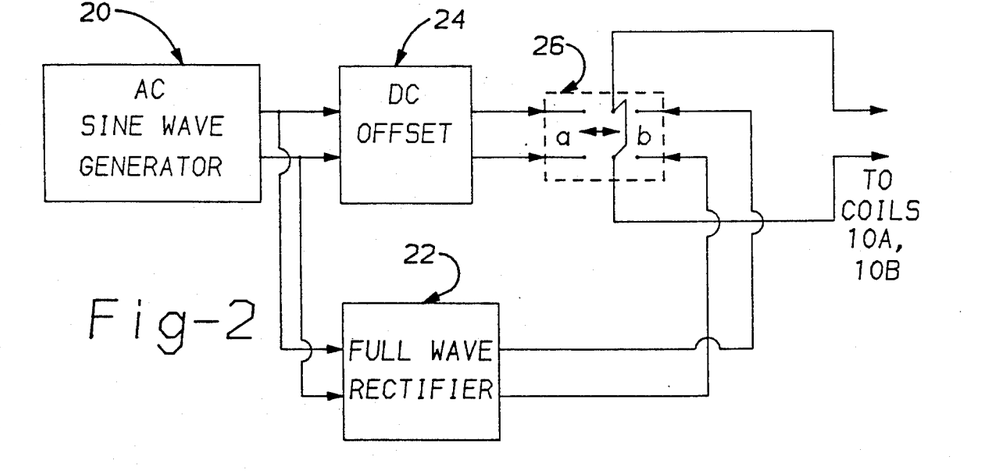
FIG. 2 is a schematic electrical diagram of a preferred form of generating apparatus used to drive the coil shown in FIG. 1 and the signal shapes employed.
Figure 2A:
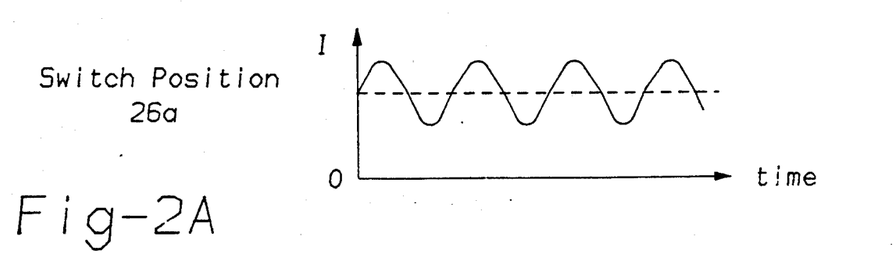
FIGS. 2A-2D are diagrams of signal waveshapes generated by the apparatus shown in FIG. 2.
Figure 2B:
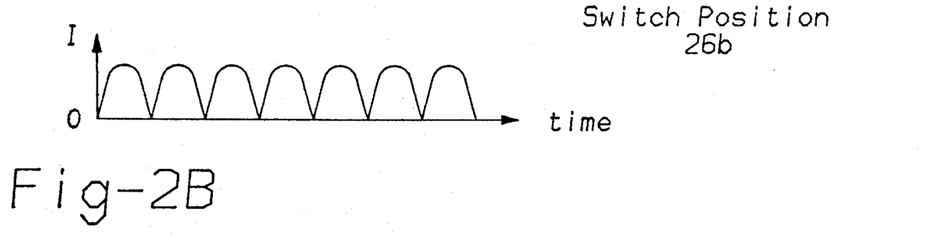

Referring to FIG. 2, coils 10A and 10B receive electrical signals from a conventional AC sine wave generator 20 connected by means of a switch 26 either to a DC offset network 24 or to a full wave rectifier 22. The instantaneous current I supplied to coils 10A and 10B as a function of time t is shown for both switch positions 26a and 26b in FIGS. 2A and 2B, respectively. Similarly, the instantaneous magnetic flux density $B_o$ produced within active volume 14 is depicted as a function of time for both switch positions 26A and 26B in FIGS. 2C and 2D, respectively. The frequency and amplitude of the signals generated by circuits 20, 22 and 24 are explained later in detail.

Cell 12 contains a specific complement of intrinsic ionic species and is surrounded by a liquid or tissue medium containing ionic species required for cell and tissue function. TABLE 1 lists a typical, but incomplete, group of such ionic species suitable for use with the invention and shows the charge-to-mass ratio (q/m) of each species, in units of Coulombs per kilogram, as well as a preferred repetition rate or frequency ($f_c$), in Hz, for each species, for the specific case in which the magnetic flux density is $5 \times 10^{-5}$ Tesla. For any other ionic species not indicated in TABLE 1, or for any magnetic flux density other than $5\times 10^{-5}$ Tesla, the preferred frequency is found using the Cyclotron Resonance Relationship.

TABLE 1

| Ionic Species | $\left(\dfrac{q}{m}\right)$, Coulombs per Kilogram | $(f_c)$,* Hz |
|---|---|---|
| Hydrogen, H+ | $95.6 \times 10^6$ | 761 |
| Lithium, Li+ | $13.9 \times 10^6$ | 111 |
| Magnesium, Mg++ | $7.93 \times 10^6$ | 63.1 |
| Calcium, Ca++ | $4.81 \times 10^6$ | 38.3 |
| Sodium, Na+ | $4.19 \times 10^6$ | 33.3 |
| Chlorine, Cl− | $2.72 \times 10^6$ | 21.6 |
| Potassium, K+ | $2.46 \times 10^6$ | 19.6 |
| Bicarbonate, HCO3− | $1.57 \times 10^6$ | 12.5 |

*Resonance frequency at $5 \times 10^{-5}$ Tesla.

Figure 2C:
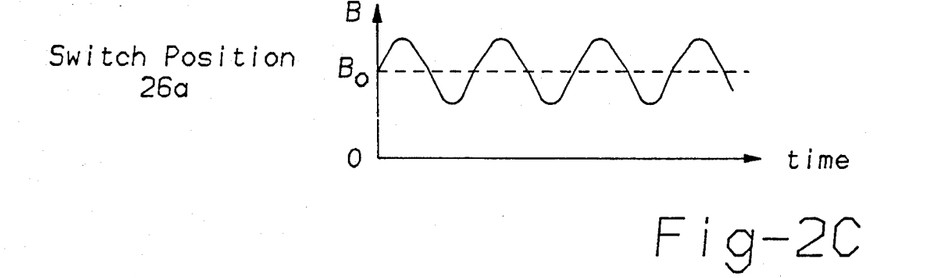
Figure 2D:
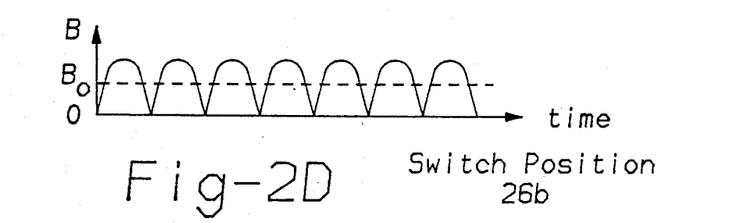

When coils 10A and 10B are energized by the apparatus shown in FIG. 2, the coils generate a magnetic flux density within active volume 14 that varies with time as shown in FIGS. 2C and 2D. A nonzero average magnetic flux density $B_o$, uniform throughout the active volume, results either from an offset sinusoidal signal or from a full-wave rectified signal applied to coils 10A and 10B.

Figure 3A:
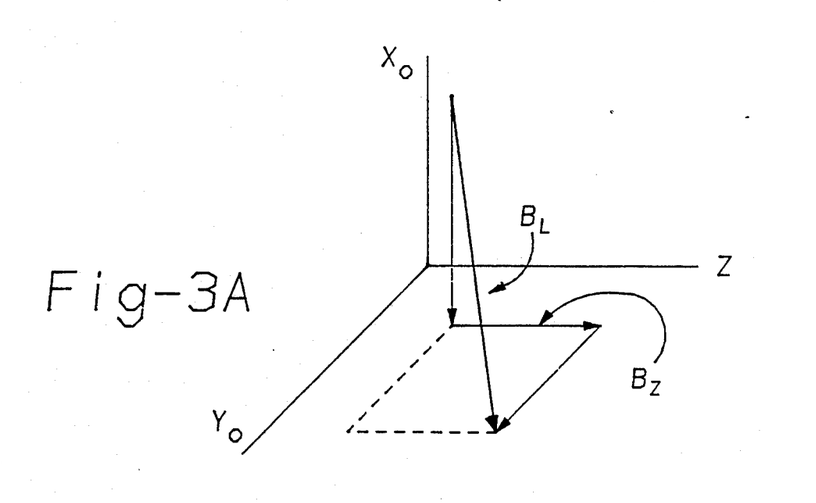
FIGS. 3A and 3B are schematic diagrams of an active volume containing an exemplary living cell located in a space defining a rectangular coordinate axis system, showing the combination of magnetic flux densities created by a pair of electrical coils and by the local magnetic field.

Referring to FIG. 3A, the local constant magnetic flux density $B_L$ will in general be superposed on the applied magnetic flux density $B_o$ generated by coils 10A and 10B in active volume 14. The local flux density $B_L$ will have three rectangular components, one of which is a component along the direction of the Z-axis. The effect of the Z-component of the local flux density will be to change the nonzero average magnetic flux density $B_o$ created by coils 10A and 10B within active volume 14 to a different net average value $B_1$.

For purposes of illustration, in order to transfer calcium ions across the membrane of cell 12, sine wave generator 20 and either offset circuit 24 or full wave rectifier 22 are regulated such that the charge-to-mass ratio for the Ca++ ion equals the ratio of the supplied frequency $f_c$ to the resultant average magnetic flux density $B_1$ times $2\pi$. Referring to FIG. 2, the frequency supplied to coils 10A and 10B will change depending on switch 26. Assuming sine wave generator 20 has an amplitude that creates an average flux density in active volume 14 which, when combined with the Z-components of the local magnetic flux density, produces a net average value of $B_1$ equal to $5\times 10^{-5}$ Tesla, the frequency of the sine wave generator should be set, for switch position 26a, to 38.3 Hz. If one chooses switch position 26b, the frequency of the sine wave generator should be set to (38.3/2) Hz, because rectifier 22 doubles the frequency output of the sine wave generator.

The resultant nonzero average magnetic flux density $B_1$ can be adjusted for maximum ion transfer in two ways; first, without adjusting the local magnetic field $B_z$, and second, by separately reducing $B_z$ to zero. The first case has already been described, wherein sine wave generator 20 is regulated to create, via coils 10A and 10B, magnetic flux density $B_o$, which when added to $B_z$, results in $B_1$. In the second case, $B_z$ can be separately reduced to zero with a simple set of coils or a permanent magnet array, and sine wave generator 20 regulated to create, via coils 10A and 10B, a magnetic flux density $B_o$ already equal to the desired flux density $B_1$.

Figures 4, 5, 6:
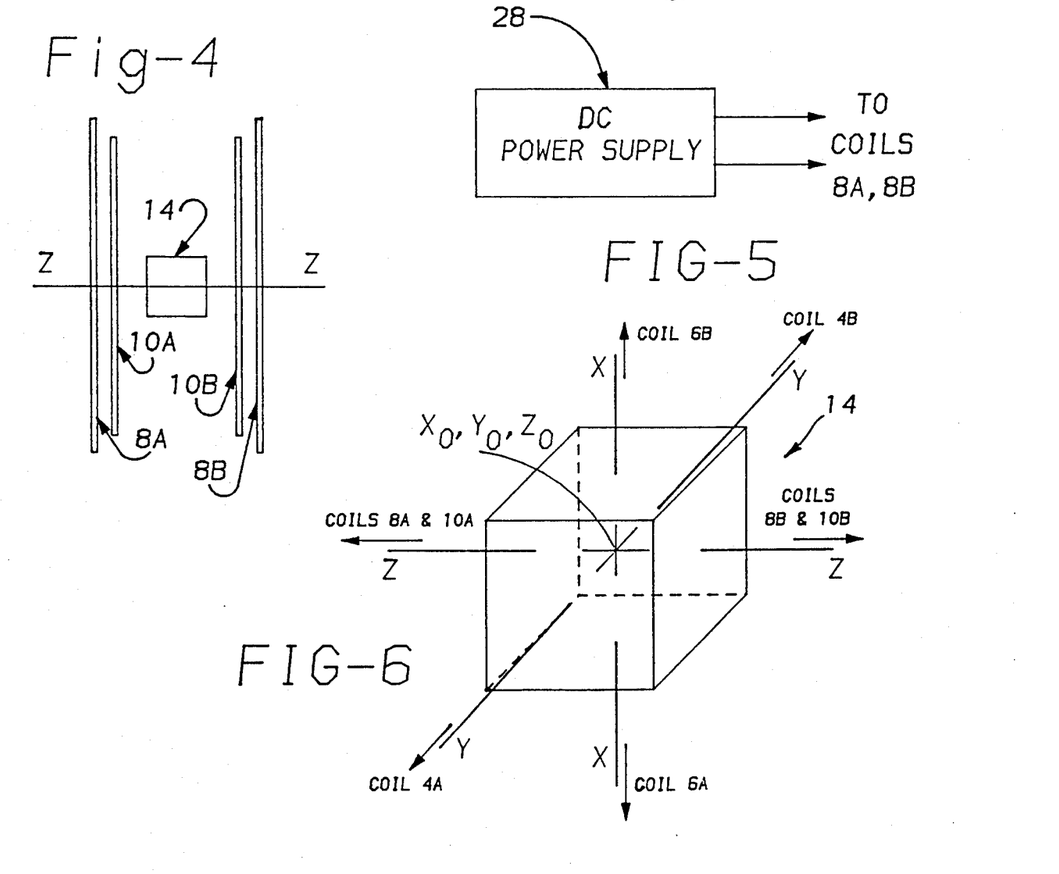
FIG. 4 is a schematic, perspective view of another exemplary living cell located in a space defining a rectangular coordinate axis system and subjected, within a bounded active volume, to a magnetic flux density created by a pair of electrical coils, or by an equivalent combination of sources of magnetic fields, such as a permanent magnetic and/or the earth's geomagnetic field.
FIG. 5 is an electrical, schematic diagram of a preferred form of signal generating apparatus used to drive the coil shown in FIG. 4.
FIG. 6 is a schematic, perspective view of the active volume surrounding an exemplary living cell located in a space defining a rectangular coordinate axis system and subjected, within this active volume, to a magnetic flux density created by three pairs of electrical coils, or an equivalent combination of sources of magnetic fields, such as permanent magnets and/or the earth's magnetic field.

Referring to FIG. 4, one example of the manner in which the local magnetic field $B_z$ can be reduced to zero is illustrated. This is achieved by means of additional Helmholtz coils 8A and 8B having $N_2$ turns of wire in each loop, with the loop diameter $2R_2$ and the separation of the midplanes of each loop equal to $R_2$. Coils 8A and 8B have their axis colinear with that of coils 10A and 10B, and coincident with the Z-axis.

Referring to FIG. 5, coils 8A and 8B are energized by a DC power supply 28. When coils 8A and 8B are energized in the manner described, they create in active volume 14 a unipolar constant magnetic flux density directed along the Z-axis such that the local magnetic field in the Z-direction ($B_z$) can be enhanced or decreased, and in particular, can be reduced to zero.

Figure 3B:
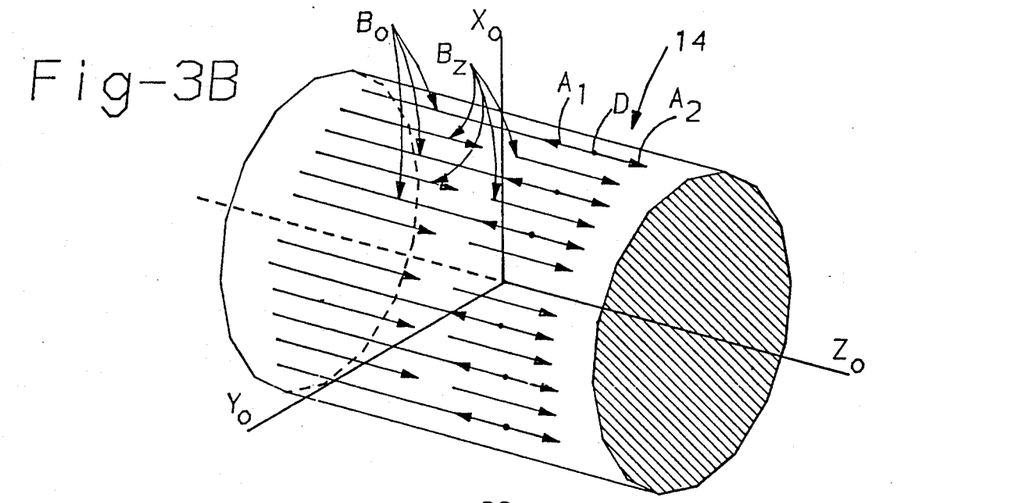

The apparatus shown in FIG. 4 also can be used to generate a nonzero unipolar resultant flux density $B_1$ if coils 8A and 8B are energized with a constant DC current that does not cancel the local magnetic field $B_z$, and coils 10A and 10B are energized by an AC current, such as the current generated by AC sine wave generator 20, having the frequency described in connection with FIG. 2. The DC current creates a unipolar magnetic field represented by arrows $B_z$ in FIG. 3B having a constant magnitude, and the AC current creates a bipolar magnetic field having periodically opposed directions that reverse at the same rate as the AC current and having a magnitude that varies at the same rate as the AC signal.

Figure 6A:
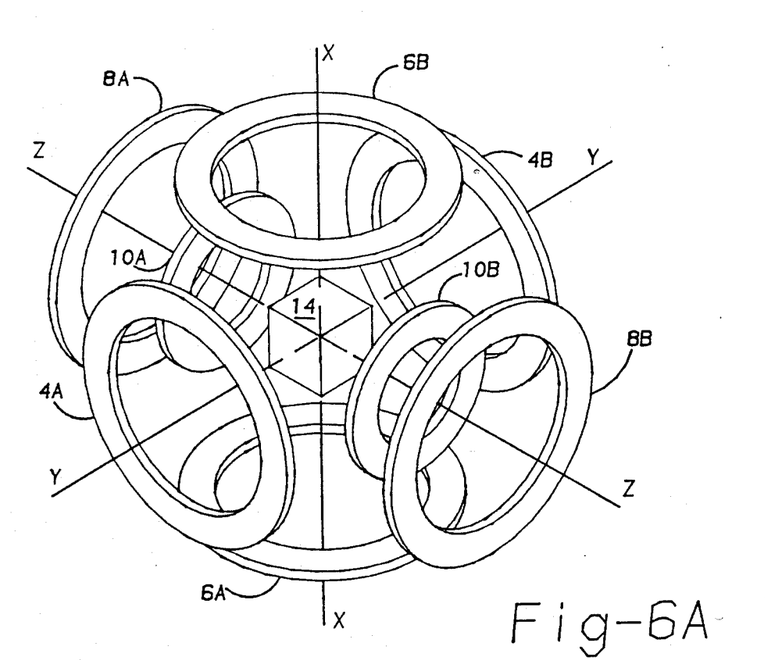
FIG. 6A is a schematic, perspective view of a preferred form of coil pairs used to subject the active volume shown in FIG. 6 to magnetic waves.

FIG. 6 illustrates active volume 14 corresponding to a coil array in which a substantially constant field magnitude having a uniformly changing direction can be used to enhance the transfer of a selected ionic species across cell membranes. As shown in FIG. 6A, coils 8A, 8B, 10A and 10B are oriented in the same manner as shown in FIGS. 1 and 4. The local magnetic flux density in the direction of Z ($B_z$) is either reduced to zero by creating an opposite but equal field via coils 8A and 8B as shown in FIG. 4, or is added to, via coils 10A and 10B, to produce an overall net nonzero flux density $B_1$ in the Z-direction. Coils 4A, 4B, 6A and 6B are arranged such that their axes are perpendicular to each other and to Z. Coils 4A and 4B have their axis along the Y coordinate axis and coils 6A and 6B have their axis along the X coordinate direction. Coils 4A, 4B, 6A, 6B, 8A, 8B, 10A and 10B are all deployed symmetrically about the $X_oY_o$ intersection on the Z-axis and each coil pair has the same physical properties described previously, that is, a sufficient number of turns, a sufficient separation between loop midplanes, a loop diameter equal to twice this separation, and a sufficient gauge of wire, all properties chosen to (1) match the impedance and current capacity of the power supply, (2) provide an adequate level of magnetic flux density, consistent with the requirements of this invention, and (3) provide the desired active volume to expose a predetermined quantity of cells and tissue to the combined magnetic flux densities created by these coils.

Figures 6B, 6C:
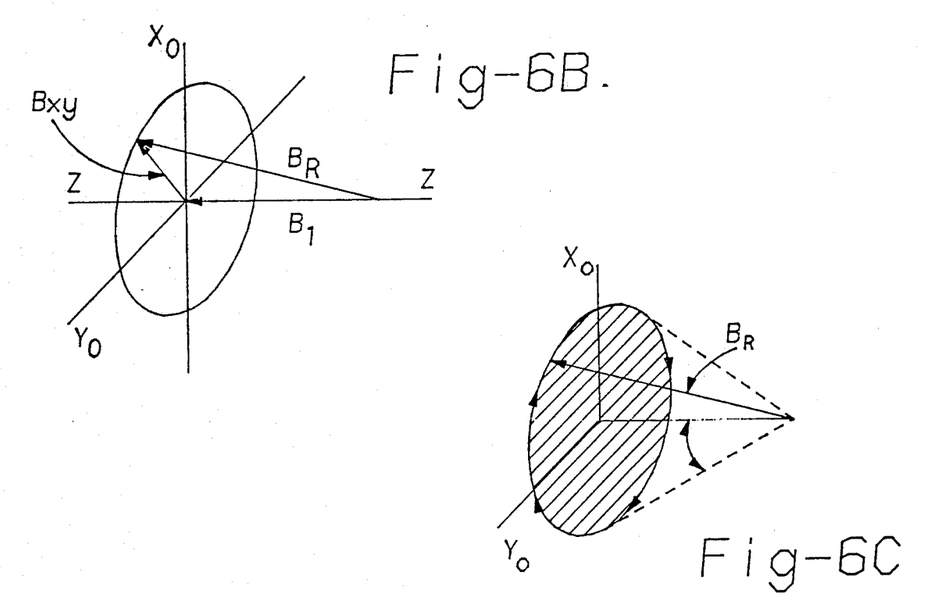
FIGS. 6B and 6C are vector diagrams illustrating a preferred form of magnetic flux density located within the active volume shown in FIG. 6.

Referring to FIG. 6, one example of operation is to align the Z-axis of the coil system with the direction of the local magnetic field and use power supply 28 and coils 8A and 8B to reduce the local magnetic flux density to zero. A rotating magnetic field $B_{xy}$ is created by the joint action of coils 4A and 4B and 6A and 6B and another field $B_1$ is created by coils 10A and 10B. As $B_{xy}$ rotates in the $X_oY_o$ plane, the net magnetic flux density resulting from the superposition of magnetic fields by coils 4A, 4B, 6A, 6B, 10A and 10B within active volume 14 is the resultant $B_R$, the direction of which sweeps out a cone, as indicated in FIG. 6B.

Figures 7, 7A, 7B, 7C:
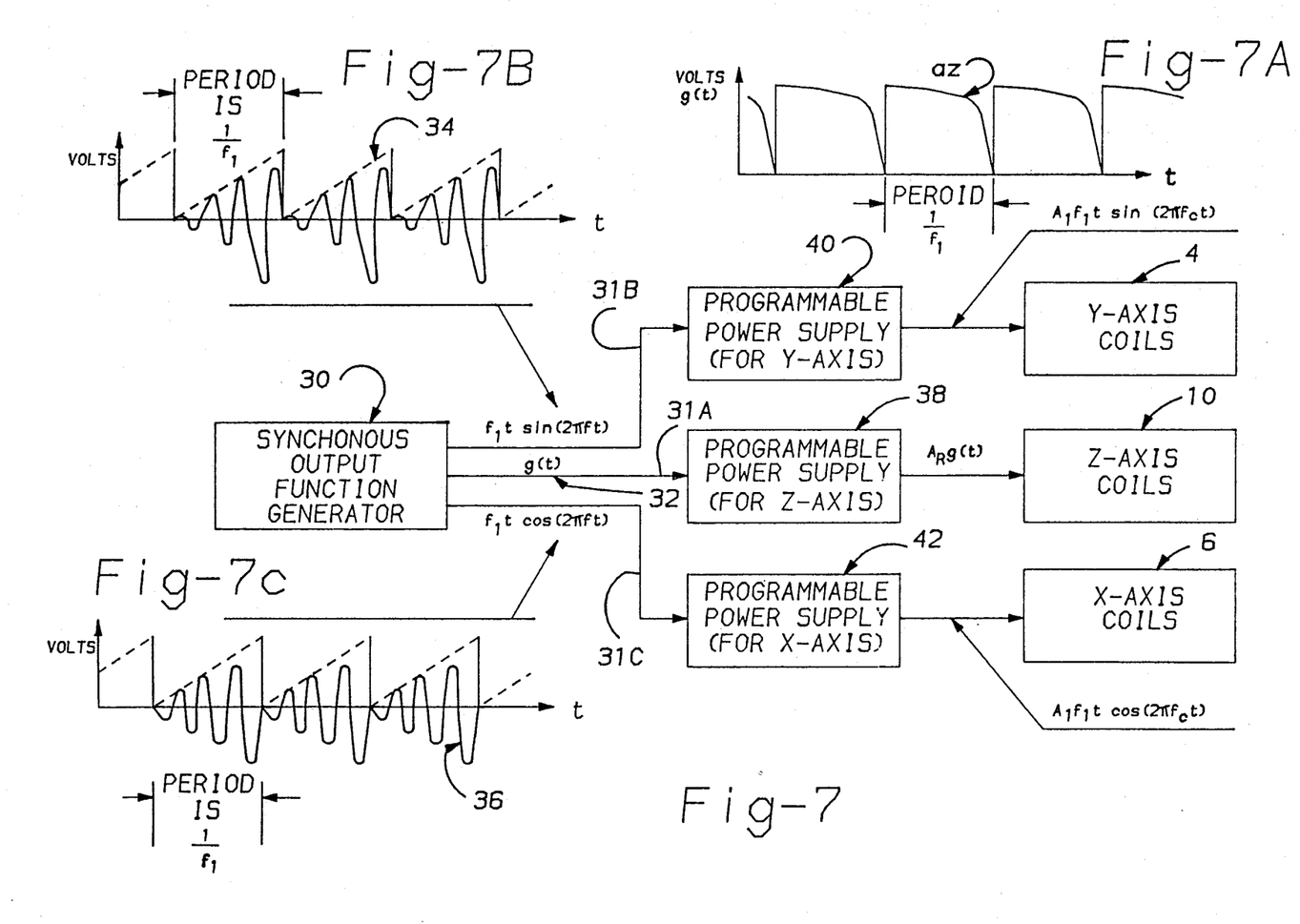
FIG. 7 is a schematic electrical diagram of a typical signal generating apparatus used to drive the coils in FIG. 6.
FIGS. 7A–7C are diagrams of signal waveshapes generated by the apparatus shown in FIG. 7.

Referring to FIG. 7, coils 4A, 4B, 6A, 6B, 10A and 10B are driven by a function generator 30 that generates three synchronous outputs, a special voltage function g(t) 32 at frequency $f_1$ (FIG. 7A) that is generated on a conductor 31A (FIG. 7), a sinusoidal signal 34 at frequence $f_c$, modulated by a ramp function (sawtooth voltage) at frequence $f_1$ (FIG. 7B) that is generated on a conductor 31B (FIG. 7), and a cosine signal 36 at frequency $f_c$, 90° out of phase with signal 34, and modulated by a ramp function at frequency $f_1$ (FIG. 7C) that is generated on a conductor 31C (FIG. 7). These three synchronous outputs from generator 30, in turn, drive three programmable power supplies 38, 40 and 42. The frequence $f_1$ is determined by the relation $f_c = cf_1$, where c is a large integer (i.e., an integer greater than or equal to 20). The frequence $f_c$ is the Cyclotron Resonance Relationship frequency $f_c$ for the magnetic flux density having the magnitude $B_R$, when one wishes to transfer ions having charge-to-mass ratio q/m across membranes located in active volume 14. Thus, to transfer calcium ions when $B_R = 5 \times 10^{-5}$ Tesla, $f_c$ will be set in generator 30 to the frequency 38.3 Hz and a typical value for $f_1$ will be 0.383 Hz (i.e., c=100).

Referring to FIG. 7, the period (or cycle time or modulation time) for each of the three outputs driving power supplies, 38, 40 and 42 will be $(1/f_1)$ seconds. In the example given in which $f_1 = 0.383$ Hz, the modulation period for the signals supplied to coils 4A, 4B, 6A, 6B, 10A and 10B is 2.61 seconds.

Power supply 40 is fed by a signal which (over one period) varies in time as the function $f_1 \sin(2\pi f_c t)$, where t is the time, given as zero seconds at the beginning of each period. Power supply 42 is fed by a signal which over one period varies as the function $f_1 t \cos(2\pi f_c t)$. Referring to FIG. 7, if $A_1$ is the amplification of power supplies 40 and 42, the signal strength driving the Y-axis coils 4A and 4B over one period is $A_1 f_1 t \sin(2\pi f_c t)$ and the corresponding signal strength driving the x-axis coils 6A and 6B is $A_1 f_1 t \cos(2\pi f_c t)$. When energized in the manner indicated, coils 4A, 4B, 6A and 6B generate a magnetic field that rotates in time at the frequency $f_c$ within the plane defined by axes $X_o$ and $Y_o$, as illustrated in FIG. 6B. Since the local magnetic flux density has been cancelled via coils 8A and 8B, the resultant magnetic field $B_R$ equals the square root of the sum of the squares of the magnetic field created by coils 10 along the Z-axis and the magnitude of the magnetic vector that rotates in time in the $X_o Y_o$ plane. The rotating vector is designated by $B_{xy}$.

To cover all possible ion channels located in the active volume 14, the value of $B_{xy}$ increases linearly in time, following the modulating function $A_1 f_1 t$, until the maximum signal occurs at $t = 1/f_1$ seconds, whereupon the entire process repeats. At any instant of time, the resultant magnetic field is $$B_R = (B_1^2 + B_{xy}^2)^{\frac{1}{2}}$$

Inasmuch as it is desirable to maintain the Cyclotron Resonance Relationship as given in TABLE 1 for the purposes of this invention, it is also desirable to maintain $B_R$ constant in magnitude over the course of this process. An ideal condition in this regard is shown in FIG. 6C, in which $B_R$ describes a cone in space, the half-angle of which will increase over one period from 0° to any angle equal to or less than 180°, during which time $B_R$ remains constant in magnitude. Because the value $B_{xy}$ increases in time, it is necessary to decrease $B_1$ synchronously in order to hold $B_R$ constant. The output of generator 30 to power supply 38 is designed to vary in time in such a manner as to reduce the field $B_1$ created by coils 10A and 10B by the proper factor required to maintain $B_R$ constant over the entire period. Referring to FIG. 7, the input 32 to power supply 38 is g(t) and the amplification of power supply 38 is $A_R$, resulting in a driving signal to coils 10A and 10B equal to $A_R g(t)$. Over one period, starting at time t equals zero seconds, the function g(t) is given by $$g(t) = (1 - f_1^2 t^2)^{\frac{1}{2}}$$

In the practice of this invention, the values of amplification of power supplies 38, 40 and 42, corresponding respectively to $A_1$, $A_1$ and $A_R$, are selected primarily with an eye towards convenience in producing a required $B_R$.

If coils 8A and 8B do not cancel the local field $B_Z$, such that the magnetic flux density along the Z-axis is not merely that produced by coils 10A and 10B, but includes an extra local component $B_Z$, the process pertinent to FIGS. 6 and 7 remains unchanged, except that the magnetic field $B_1$ is in part produced by coils 10A and 10B. Over the course of one modulation period, the angle between the Z-axis and the resultant magnetic field $B_R$ increases so that the tip of the vector sweeps out an ever-increasing circle, but the magnitude of the resultant vector remains constant since $B_1$ is being decreased at the same time. Thus, over one modulation period, the tip of the resultant magnetic field vector $B_R$ traces out some portion of a hemisphere, depending on how large the angle between the Z-axis and $B_R$ is allowed to become. The locus of points traced out by $B_R$ can cover a complete sphere by reducing $B_1$ below zero. By adjusting the value of large integer c, vector $B_R$ can be tuned to complete the generation of a hemisphere or a sphere or any fraction thereof at a specified rate. In this way, all directions for variously oriented membrane surfaces will be covered by $B_R$ in a repetitive and efficacious manner, thereby allowing the Cyclotron Resonance Relationship for enhanced permeability of ions to be met for elements of each membrane and ion channels that have various orientations. In this mode the frequency $f_c$ corresponds to the Cyclotron Resonance Relationship frequency $f_c$.

Coincidentally, a second, alternate mode of application is possible, in that the arrangement in FIGS. 6 and 7 can also be used to simultaneously enhance the transfer of two distinctly different ionic species. In this mode, $f_c$ will correspond to the Cyclotron Resonance Relationship frequency for one species and $f_1$ to the Cyclotron Resonance Relationship frequency for another. Thus, consider TABLE 1 in which the resonance frequency for hydrogen ions is 761 Hz and the resonance frequency for potassium ions is 19.6 Hz for a magnetic flux density equal to $5 \times 10^{-5}$ Tesla. If coils 6A, 6B, 8A, 8B, 10A and 10B are energized to create a field $B_R$ equal to $5 \times 10^{-5}$ Tesla in the active volume 14, and if $f_1$ is adjusted to 19.6 Hz, then choosing factor c to be 39 results in a frequency $f_c$ substantially the same as required to enhance hydrogen ion transfer. The result of this procedure will be to simultaneously enhance the transfer of both hydrogen and potassium ions across membrane surfaces within active volume 14.

Those skilled in the art will recognize the embodiments described herein may be modified or altered without departing from the true spirit and scope of the invention as defined in the appended claims. For example, the linear axes shown in the drawing may have more complicated paths, or the axes may be oriented along planes other than the conventional XYZ planes, or the size, shape and physical properties of the coils may be altered, or the coils may take forms other than Hemholtz coils, such as solenoids, wires and sheets, or the coils may be replaced by equivalent devices for producing the required flux densities. The ions may be put into cyclotron resonance in a wide variety of ways as long as the relationship between the charge-to-mass ratio and the frequency and magnetic flux density is maintained. For some applications, appropriate mechanical signals may be substituted for the described electrical signals.

What is claimed is:

1. Apparatus for regulating the permeability of a predetermined ion having a predetermined charge-to-mass ratio through a membrane located in a space subjected to a local static magnetic field, the space defining at least one reference path passing through the membrane, the reference path extending in a first direction and also extending in a second direction opposite the first direction, said apparatus comprising:

field creating means responsive to signals for creating a magnetic field which, when combined with the local magnetic field, results in a resultant magnetic field having a flux density with at least one component representable by a component vector having a direction extending in the first direction along the path and having a magnitude that fluctuates at a predetermined rate to create a nonzero average value, wherein the ratio of the predetermined rate to the nonzero average value is a function of the charge-to-mass ratio of the predetermined ion; and signal generating means for generating said signals, at least some of said signals being generated at the predetermined rate.

2. Apparatus, as claimed in claim 1, wherein the signals are electrical signals.

3. Apparatus, as claimed in claim 2, wherein:
(A) the resultant magnetic field comprises
   (1) a unipolar magnetic field having a flux density with at least one unipolar component representable by a unipolar vector having a direction extending in the first direction along the path and having a substantially constant magnitude; and
   (2) a bipolar magnetic field having a flux density with at least one bipolar component representable by a bipolar vector having periodically opposed directions that reverse at the predetermined rate and that extend along the path, said bipolar component having a magnitude that varies at the predetermined rate; and
(B) the signal generating means comprises
   (1) means for generating a direct current signal for creating the unipolar magnetic field, and
   (2) means for generating an alternating current signal for generating the bipolar magnetic field.

4. Apparatus, as claimed in claim 3, wherein the signal generating means comprises means for tuning the electrical signals so that the charge-to-mass ratio of the predetermined ion is substantially equal to $2\pi$ times the ratio of the predetermined rate to the flux density magnitude of the unipolar vector.

5. Apparatus, as claimed in claim 3, wherein the ratio of the predetermined rate to the flux density magnitude of the unipolar vector is substantially between $152.5 \times 10^5$ and $2.50 \times 10^5$, where the predetermined rate is measured in Hertz and the flux density is measured in Tesla.

6. Apparatus as claimed in claim 2, wherein the resultant magnetic field comprises a unipolar magnetic field having a flux density with at least one unipolar component represented by a unipolar vector having a direction extending in a first direction along the path and having a magnitude that varies at the predetermined rate.

7. Apparatus, as claimed in claim 6 wherein the signal generating means comprises means for generating an alternating current signal offset by a predetermined DC level.

8. Apparatus, as claimed in claim 6, wherein the signal generating means comprises means for generating an alternating current signal and means for rectifying the alternating current signal.

9. Apparatus, as claimed in claim 6, wherein the signal generating means comprises means for tuning the electrical signals so that the charge-to-mass ratio of the predetermined ion is substantially equal to $2\pi$ times the ratio of the predetermined rate to the average value of the flux density magnitude of the unipolar vector.

10. Apparatus, as claimed in claim 6, wherein the ratio of the predetermined rate to the average value of the flux density magnitude of the unipolar vector is substantially between $152.5 \times 10^5$ and $2.50 \times 10^5$, where the predetermined rate is measured in Hertz and the flux density is measured in Tesla.

11. Apparatus, as claimed in claim 2, wherein:
(A) the resultant magnetic field comprises a unipolar magnetic field having a flux density with at least one unipolar component representable by a unipolar vector having
   (1) a direction extending only in the first direction along the path, and
   (2) a magnitude fluctuating at the predetermined rate; and
(B) the signal generating means comprises means for generating a direct current having a magnitude that fluctuates at the predetermined rate.

12. Apparatus, as claimed in claim 2, wherein:
(A) the resultant magnetic field comprises a magnetic field having a flux density with at least one component representable by a vector having
   (1) a direction that sweeps across the path at the predetermined rate, and
   (2) a substantially constant magnitude; and
(B) the signal generating means comprises means for generating signals, whereby the resultant magnetic field rotates.

13. Apparatus, as claimed in claim 12, wherein the signal generating means comprises means for generating signals that differ in phase by substantially 90 degrees.

14. Apparatus, as claimed in claim 13, wherein:
said space defines first and second intersecting coordinate axes lying in a first plane and a third coordinate axis perpendicular to the first plane and passing through the point of intersection of the first and second axes;
the resultant magnetic field comprises a magnetic field having a flux density with at least one component representable by a vector having a direction that passes through said point of intersection and precesses around said third coordinate axis to define a cone, the rate at which the angle between the vector and the first plane changes being proportional to the predetermined rate; and the signal generating means comprises:

(A) means for generating a first AC signal having a first predetermined phase angle, a second AC signal having a second predetermined phase angle substantially 90 degrees out of phase with the first phase angle in order to create a component of a magnetic field that rotates in the first plane, and a DC signal; and (B) means for synchronously modulating the said first AC signal, the said second AC signal and the said DC signal, each signal simultaneously fluctuating at the said predetermined rate.

15. Apparatus, as claimed in claim 12, wherein the signal generating means comprises means for tuning the electrical signals so that the charge-to-mass ratio of the predetermined ion is substantially equal to $2\pi$ times the ratio of the predetermined rate to the average flux density magnitude of the unipolar vector in the first direction.

16. Apparatus, as claimed in claim 12, wherein the ratio of the predetermined rate to the average flux density magnitude of the unipolar vector in the first direction is substantially between $152.5 \times 10^5$ and $2.50 \times 10^5$, where the predetermined rate is measured in Hertz and the flux density is measured in Tesla.

17. Apparatus, as claimed in claim 2, wherein the signal generating means comprises means for tuning the electrical signals so that the charge-to-mass ratio of the predetermined ion is substantially equal to $2\pi$ times the ratio of the predetermined rate to the nonzero average value.

18. Apparatus as claimed in claim 2, wherein the ratio of the predetermined rate to the average nonzero magnitude of flux density is substantially between $152.5 \times 10^5$ and $2.50 \times 10^5$, where the predetermined rate is measured in Hertz and the flux density is measured in Tesla.

19. Apparatus, as claimed in claim 2, wherein the predetermined ion is any ionic species having a predetermined charge-to-mass ratio.

20. Apparatus, as claimed in claim 2, wherein the predetermined ions are selected from a group consisting of H+, Li+, Mg$^{2+}$, Ca$^{2+}$, Na+, K+, Cl− and HCO$_3$−.

21. A method of regulating the permeability of a predetermined ion having a predetermined charge-to-mass ratio through a membrane located in a space subjected to a local magnetic field, the space defining at least one reference path passing through the membrane, the reference path extending in a first direction and also extending in a second direction opposite the first direction, said method comprising the steps of:

creating a magnetic field which, when combined with the local magnetic field, results in a resultant magnetic field having a flux density with at least one component representable by a component vector having a direction extending in the first direction along the path and having a magnitude that fluctuages at a predetermined rate to create a nonzero average value; and creating a predetermined relationship between the ratio of the predetermined rate to the nonzero value, wherein said ratio is a function of the charge-to-mass ratio of the predetermined ion.

22. A method, as claimed in claim 21, wherein the resultant magnetic field comprises:

a unipolar magnetic field having a flux density with at least one unipolar component representable by a unipolar vector having a direction extending in the first direction along the path and having a substantial constant magnitude; and a bipolar magnetic field having a flux density with at least one bipolar component representable by a bipolar vector having periodically opposed directions that reverse at the predetermined rate and that extend along the path, said bipolar component having a magnitude that varies at the predetermined rate.

23. A method, as claimed in claim 22, wherein the charge to mass ratio of the predetermined ion is substantially equal to $2\pi$ times the ratio of the predetermined rate to the flux density magnitude of the unipolar vector.

24. A method, as claimed in claim 22, wherein the ratio of the predetermined rate to the flux density magnitude of the unipolar vector is substantially between $152.5 \times 10^5$ and $2.50 \times 10^5$, where the predetermined rate is measured in Hertz and the flux density is measured in Tesla.

25. A method, as claimed in claim 21, wherein the resultant magnetic field comprises a unipolar magnetic field having a flux density with at least one unipolar component representable by a unipolar vector having:

a direction extending only in the first direction along the path; and a magnitude fluctuating at the predetermined rate.

26. A method, as claimed in claim 25, wherein the charge-to-mass ratio of the predetermined ion is substantially equal to $2\pi$ times the ratio of the predetermined rate to the average value of the flux density magnitude of the unipolar vector.

27. A method, as claimed in claim 25, wherein the ratio of the predetermined rate to the average value of the flux density magnitude of the unipolar vector is substantially between $152.5 \times 10^5$ and $2.50 \times 10^5$, where the predetermined rate is measured in Hertz and the flux density is measured in Tesla.

28. A method, as claimed in claim 21, wherein the resultant magnetic field comprises a magnetic field having a flux density with at least one component representable by a vector having a direction that sweeps across the path at the predetermined rate and having a substantially constant magnitude.

29. A method, as claimed in claim 28, wherein:

said space defines first and second intersecting coordinate axes lying in a first plane and a third coordinate axis perpendicular to the first plane and passing through the point of intersection of the first and second axes; and the resultant magnetic field comprises a magnetic field having a flux density with at least one component representable by a vector having a direction that passes through said point of intersection and precesses around said third coordinate axis to define a cone, the rate at which the angle between the unipolar vector and the first plane changes being proportional to the predetermined rate.

30. A method, as claimed in claim 28, wherein the charge-to-mass ratio of the predetermined ion is substantially equal to $2\pi$ times the ratio of the predetermined rate to the average flux density magnitude of the unipolar vector in the first direction.

31. A method, as claimed in claim 28, wherein the ratio of the predetermined rate to the average flux density magnitude of the unipolar vector in the first direction is substantially between $152.5 \times 10^5$ and $2.50 \times 10^5$, where the predetermined rate is measured in Hertz and the flux density is measured in Tesla.

32. A method, as claimed in claim 21, wherein the charge-to-mass ratio of the predetermined ion is substantially equal to $2\pi$ times the ratio of the predetermined rate to the nonzero average value.

33. A method, as claimed in claim 21, wherein the ratio of the predetermined rate to the average nonzero magnitude of flux density is substantially between $152.5 \times 10^5$ and $2.50 \times 10^5$, where the predetermined rate is measured in Hertz and the flux density is measured in Tesla.

34. A method, as claimed in claim 21, wherein the predetermined ion is any ionic species having a predetermined charge-to-mass ratio.

35. A method, as claimed in claim 21, wherein the predetermined ions are selected from a group consisting of $H+$, $Li+$, $Mg^{2+}$, $Ca^{2+}$, $Na+$, $K+$, $Cl-$ and $HCO_3^-$.

* * * * *